US011998623B2

(12) United States Patent
Hu et al.

(10) Patent No.: US 11,998,623 B2
(45) Date of Patent: Jun. 4, 2024

(54) WATER-SOLUBLE UNIDIRECTIONAL MOISTURE TRANSPORT TRADITIONAL CHINESE MEDICINE FACIAL MASK AND PREPARATION THEREOF

(71) Applicant: City University of Hong Kong, Kowloon (HK)

(72) Inventors: Jinlian Hu, Kowloon (HK); Yifan Si, Kowloon (HK); Shuo Shi, Kowloon (HK); Chunxia Guo, Kowloon (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 17/877,005

(22) Filed: Jul. 29, 2022

(65) Prior Publication Data

US 2023/0111046 A1  Apr. 13, 2023

(30) Foreign Application Priority Data

Oct. 13, 2021  (CN) .......................... 202111192818.4

(51) Int. Cl.
*A61K 8/02*  (2006.01)
*A61K 8/20*  (2006.01)
(Continued)

(52) U.S. Cl.
CPC .............. *A61K 8/0212* (2013.01); *A61K 8/20* (2013.01); *A61K 8/345* (2013.01); *A61K 8/731* (2013.01);
(Continued)

(58) Field of Classification Search
None
See application file for complete search history.

(56) References Cited

U.S. PATENT DOCUMENTS

2015/0125499 A1*  5/2015  Ochiai ..................... B32B 5/26
442/381

FOREIGN PATENT DOCUMENTS

AU  2018200406  2/2018
AU  2018271234  12/2018
(Continued)

OTHER PUBLICATIONS

CN109528615B—Google English Translation (Year: 2019).*
CN106236624A—Google English Translation (Year: 2016).*

*Primary Examiner* — Kyung S Chang
(74) *Attorney, Agent, or Firm* — Renner, Kenner, Greive, Bobak, Taylor & Weber

(57) ABSTRACT

A water-soluble unidirectional moisture transport traditional Chinese medicine facial mask and a preparation method thereof. The facial mask includes a facial mask substrate and a facial mask effective ingredient layer, wherein a lateral surface of the facial mask substrate is a hydrophobic surface, and the other lateral surface is a superhydrophilic surface; the facial mask effective ingredient layer is loaded to the superhydrophilic surface, in which facial mask effective ingredients include a traditional Chinese medicine colloid. In use, by simply spraying water, the effective ingredients such as the traditional Chinese medicine on the surface can be quickly dissolved to exert effects. Its hydrophobic layer can be kept dry, which not only delays volatilization of liquid and prolongs the effective time, but also is easy to operate and is clean and hygienic. The present invention has a simple preparation method, is non-harmful and non-toxic, low-carbon and environmentally friendly.

21 Claims, 5 Drawing Sheets

(51) Int. Cl.
*A61K 8/34* (2006.01)
*A61K 8/73* (2006.01)
*A61K 8/92* (2006.01)
*A61K 8/9789* (2017.01)
*A61K 8/9794* (2017.01)
*A61Q 19/00* (2006.01)

(52) U.S. Cl.
CPC .............. *A61K 8/735* (2013.01); *A61K 8/922* (2013.01); *A61K 8/9789* (2017.08); *A61K 8/9794* (2017.08); *A61Q 19/007* (2013.01)

(56) References Cited

FOREIGN PATENT DOCUMENTS

| CN | 106236624 A | * | 12/2016 | ........... A61K 8/0212 |
|----|-------------|---|---------|------------------------|
| CN | 109528615 B | * | 2/2021  | ............... A61K 8/44 |

* cited by examiner

WATER-SOLUBLE UNIDIRECTIONAL MOISTURE TRANSPORT TRADITIONAL CHINESE MEDICINE FACIAL MASK AND PREPARATION THEREOF

TECHNICAL FIELD

The present invention relates to the technical field of cosmetics, and in particular relates to a water-soluble unidirectional moisture transport traditional Chinese medicine facial mask and preparation thereof.

BACKGROUND

Due to convenient use and good skin care effects, facial sheet masks are widely favored by consumers and currently occupy the vast majority of the market. The traditional sheet facial masks are made of a hydrophilic substrate to which a liquid nutrient solution is adsorbed, and then encapsulated in plastic/aluminum foil packaging. In use, the sheet mask is applied to the face directly by consumers. However, the shortcomings of the traditional sheet masks are also obvious: first, a thoroughly wet facial mask not only makes the facial mask wet or messy but also makes the hands wet or messy in use; second, a large amount of nutrient solution is left in the packaging and seriously wasted; also, most of the facial mask nutrient solutions are organic solvents, which may cause skin irritation and are against the environment.

In view of these problems, the present invention develops a water-soluble unidirectional moisture transport traditional Chinese medicine facial mask.

SUMMARY

The objective of the present invention is to provide a water-soluble unidirectional moisture transport traditional Chinese medicine facial mask and preparation thereof. The water-soluble unidirectional moisture transport traditional Chinese medicine facial mask of the present invention is a dry facial mask, with one surface being hydrophobic, and the other surface being superhydrophilic and loaded with effective ingredients such as a traditional Chinese medicine colloid. In use, by simply spraying water directly on the dry facial mask, the traditional Chinese medicine effective ingredients on the superhydrophilic surface can be quickly dissolved and applied to the human face to exert effects. The outer hydrophobic layer may delay volatilization of moisture and play a certain antifouling role. It is more convenient to operate. Such dry facial mask does not consume plastic/metal packaging, which is environmentally friendly and reduces costs.

To achieve the above objectives, the present invention adopts the following technical solutions:

One aspect of the present invention provides a water-soluble unidirectional moisture transport traditional Chinese medicine facial mask, which is a dry facial mask, comprising a facial mask substrate and a facial mask effective ingredient layer;
  a lateral surface of the facial mask substrate is a hydrophobic surface, and the other lateral surface is a superhydrophilic surface;
  the facial mask effective ingredient layer is loaded to the superhydrophilic surface, in which facial mask effective ingredients comprise a traditional Chinese medicine colloid.

The facial mask of the present invention is an asymmetric unidirectional moisture transport traditional Chinese medicine facial mask, which is a dry facial mask. It is hydrophobic on one side and superhydrophilic on the other side, in which the effective ingredient layer containing the traditional Chinese medicine colloid is loaded. In use, by simply spraying water, the effective ingredients such as the traditional Chinese medicine on the surface can be quickly dissolved to exert effects. Its hydrophobic layer can be kept dry, which not only delays volatilization of liquid and prolongs the effective time, but also is easy to operate and is clean and hygienic.

The water-soluble unidirectional moisture transport traditional Chinese medicine facial mask according to the present invention, preferably, the superhydrophilic surface of the facial mask substrate is formed by electrospinning on the lateral surface of a superhydrophilic substrate; the other lateral surface of the superhydrophilic substrate is the superhydrophilic surface.

The water-soluble unidirectional moisture transport traditional Chinese medicine facial mask according to the present invention, preferably, the superhydrophilic substrate is a cellulose membrane or a superhydrophilic non-woven fabric, both of which superhydrophilic substrates may be purchased commercially; in addition, the superhydrophilic substrate may also be obtained by any other preparation method, e.g. electrospinning.

The water-soluble unidirectional moisture transport traditional Chinese medicine facial mask according to the present invention, preferably, the facial mask effective ingredients further comprise a plant essential oil, a moisturizing agent, hyaluronic acid, a surfactant and a metal salt. The water-soluble unidirectional moisture transport traditional Chinese medicine facial mask according to the present invention, preferably, the plant essential oil is one or a combination of two or more selected from the group consisting of: rose essential oil, tea tree essential oil, lavender essential oil and grapefruit essential oil.

The water-soluble unidirectional moisture transport traditional Chinese medicine facial mask according to the present invention, preferably, the moisturizing agent is one or a combination of two or more selected from the group consisting of: glycerol, butanediol and propylene glycol.

The water-soluble unidirectional moisture transport traditional Chinese medicine facial mask according to the present invention, preferably, the surfactant is one or a combination of two or more selected from the group consisting of: sodium hexadecyl sulfonate, sodium lauryl polyoxyethylene ether sulfate and coconut diethanolamide.

The water-soluble unidirectional moisture transport traditional Chinese medicine facial mask according to the present invention, preferably, the metal salt is lithium chloride and/or sodium chloride.

The water-soluble unidirectional moisture transport traditional Chinese medicine facial mask according to the present invention, preferably, the mass ratio of the traditional Chinese medicine colloid to the plant essential oil to the moisturizing agent to the hyaluronic acid to the surfactant to the metal salt is (20-40):(5-10):(2-10):1:(0.2-2):(0.5-1), e.g., 40:10:10:1:1:1, 20:10:10:1:0.5:1, and 20:10:10:1:0.5:0.5.

The water-soluble unidirectional moisture transport traditional Chinese medicine facial mask according to the present invention, preferably, the traditional Chinese medicine colloid is *Bletilla striata* gel.

Another aspect of the present invention provides a preparation method of the above water-soluble unidirectional moisture transport traditional Chinese medicine facial mask, the preparation method comprising:

forming a hydrophobic layer by electrospinning on a lateral surface of a superhydrophilic substrate;

preparing a facial mask effective ingredient layer on the other lateral surface of the superhydrophilic substrate;

heating and drying to obtain the water-soluble unidirectional moisture transport traditional Chinese medicine facial mask.

According to the preparation method of the present invention, preferably, the facial mask effective ingredient layer is prepared by electrostatic spraying. The electrostatic spraying technique allows the effective ingredients of low-molecular weight, which cannot form nanofibers, to be spread all over the substrate. This does not only save most of the raw materials, but also allow the raw materials to be spread more evenly, so as to be quickly dissolved in water subsequently to exert a medicinal effect. Compared with means of dipping, spin coating or high pressure spraying, the electrostatic spraying method does not completely wet the substrate, and may maintain the soft feel of the substrate to the greatest extent.

The effective ingredients of the facial mask of the present invention are formed into a membrane by electrostatic spraying and then made into a dry membrane. The dry membrane may be quickly dissolved in water and used on face. The consumption is small; the cost is reduced, and unnecessary loss is reduced.

Further, preparing of the facial mask effective ingredient layer comprises:

adding the facial mask effective ingredients into water to form an electrostatic spraying stock solution;

wrapping the superhydrophilic substrate on an electrostatic spraying roller with the superhydrophilic surface facing outward, and electrostatically spraying the electrostatic spraying stock solution on the superhydrophilic surface of the superhydrophilic substrate to prepare the facial mask effective ingredient layer.

In the preparation process of the facial mask effective ingredient layer, preferably, the mass ratio of metal salt in the facial mask effective ingredients to water is (0.5-1):200, e.g., 1:200. That is, the mass ratio of the traditional Chinese medicine colloid to the plant essential oil to the moisturizing agent to the hyaluronic acid to the surfactant to the metal salt to the water is (20-40):(5-10):(2-10):1:(0.2-2):(0.5-1):200, e.g., 40:10:10:1:1:1:200, 20:10:10:1:0.5:1:200, and 20:10:10:1:0.5:0.5:200.

It should be guaranteed that the content of each effective ingredient in the facial mask effective ingredient layer allows it to exert effects without affecting the electrospinning performance of the solution. In addition, the price and cost factors are also considered. The metal salt may effectively improve the spinnability, but if the content of the metal salt is too high, fibers will be too thick, so the content of the metal salt should not be too high.

In the preparation process of the facial mask effective ingredient layer, preferably, the electrostatic spraying is performed by a single-needle electrostatic spraying device.

In the preparation process of the facial mask effective ingredient layer, preferably, conditions of the electrostatic spraying comprise: a voltage of 18-30 kV, an injection pump flow rate of 0.1-0.4 mL/h, and a receiving distance of 5-15 cm.

According to the preparation method of the present invention, preferably, preparation of the hydrophobic layer comprises:

adding a hydrophobic high-molecular polymer and a metal salt into a dimethylformamide (DMF) and/or tetrahydrofuran solvent, in which a superhydrophobic powder is dispersed to obtain a spinning stock solution;

wrapping the superhydrophilic substrate on a roller, and preparing the hydrophobic layer by electrospinning the spinning stock solution on the superhydrophilic substrate.

In the preparation process of the hydrophobic layer, the addition of the hydrophobic high-molecular polymer is to form a hydrophobic membrane, so that it has the ability of unidirectional moisture transport. The addition of the metal salt improves the spinnability of the hydrophobic high-molecular polymer. The addition of the superhydrophobic powder may further improve the hydrophobicity of the polymer membrane, and also improve its ability of unidirectional moisture transport. If no superhydrophobic powder is added, it still has the ability of unidirectional moisture transport, but the effect is reduced.

In the preparation process of the hydrophobic layer, preferably, the electrospinning is performed by a single-needle spinning device.

In the preparation process of the hydrophobic layer, preferably, conditions of the electrospinning comprise: a voltage of 18-26 kV, an injection pump flow rate of 0.1-0.4 mL/h, and a receiving distance of 10-15 cm.

In the preparation process of the hydrophobic layer, preferably, the hydrophobic high-molecular polymer is polyurethane (TPU) and/or polyvinylidene fluoride (PVDF).

In the preparation process of the hydrophobic layer, preferably, the metal salt is lithium chloride and/or sodium chloride.

In the preparation process of the hydrophobic layer, preferably, the superhydrophobic powder is superhydrophobic silica aerogel powder or stearic acid-magnesium oxide powder; wherein the superhydrophobic silica aerogel powder is fluorinated silica aerogel or silica aerogel containing a group such as a long carbon chain.

In the preparation process of the hydrophobic layer, preferably, the mass ratio of the hydrophobic high-molecular polymer to the superhydrophobic powder to the metal salt to the solvent is (2-5):(0-4):(0.05-0.2):20, e.g., 5:1:0.1:20, 3:4:0.1:20, 4:2:0.1:20, and 2:4:0.2:20.

In the preparation process of the hydrophobic layer, the spinnability is the best when the concentration of the hydrophobic high-molecular polymer is within the limited range. The content of the superhydrophobic powder should not be too high; otherwise, the hydrophobicity of the hydrophobic membrane will be too high, thus affecting the ability of unidirectional moisture transport. The metal salt improves the spinnability of the hydrophobic high-molecular polymer, but if the content of the metal salt is too high, the electrospun fibers will be too thick, etc.

In a preferred embodiment, the preparation process of the spinning stock solution includes: adding hydrophobic high-molecular polymer particles and a metal salt into a dimethylformamide (DMF) organic solvent, and stirring at 40-60° C. for 2-5 h; then dispersing a superhydrophobic powder in the resulting solution, ultrasonically dispersing for 20-60 min, and then stirring at room temperature for 1-2 h to finally obtain a high-viscosity and transparent spinning stock solution, which is placed at room temperature for later use.

In a preferred embodiment, the process of preparing the hydrophobic layer by electrospinning includes: winding a superhydrophilic substrate as a collecting substrate on a roller, collecting the spinning stock solution on the superhydrophilic substrate under a high voltage of 18-26 kV by means of a single-needle spinning device, preparing and obtaining the hydrophobic layer; wherein the injection pump flow rate is set as 0.1-0.4 mL/h, the receiving distance is 10-15 cm, and the spinning time is 10-180 min; and finally, removing it from the roller, and placing it at room temperature for later use.

In a preferred embodiment, the preparation process of the electrostatic spraying stock solution includes: dispersing a traditional Chinese medicine colloid, a plant essential oil, a moisturizing agent, hyaluronic acid, a surfactant and a metal salt in distilled water, and stirring at room temperature for 1-5 h to obtain the electrostatic spraying stock solution.

In a preferred embodiment, the process of preparing the facial mask effective ingredient layer by electrostatic spraying and heating and drying include: wrapping the opposite side of the superhydrophilic substrate with the hydrophobic layer on an electrostatic spraying roller, with the superhydrophilic surface facing outward; collecting the electrostatic spraying stock solution on the superhydrophilic surface under a high voltage of 12-30 kV by means of a single-needle spinning device, preparing and obtaining an electro-sprayed layer containing traditional Chinese medicine ingredients, i.e., the facial mask effective ingredient layer; wherein the injection pump flow rate is set as 0.1-0.4 mL/h, the receiving distance is 5-15 cm, and the spraying time is 5-120 min; and finally, removing the entity from the roller and placing it in an oven at 60° C. for 24-48 h for drying. According to the preparation method of the present invention, preferably, the drying temperature is 40-60° C., e.g., 60° C. A drying temperature that is too high may result in damage to the polymer membrane.

According to the preparation method of the present invention, preferably, the drying is performed for 24-48 h.

The water-soluble unidirectional moisture transport traditional Chinese medicine facial mask provided by the present invention is a dry facial mask, which may avoid the use of plastic/metal packaging, and is environmentally friendly and lightweight. In use, by simply spraying water, the traditional Chinese medicine effective ingredients can be quickly dissolved and used on human face to exert effects. The hydrophobic surface is convenient and hygienic to operate, and may also delay volatilization of liquid, reduce the consumption of water, and prolong the effective time of the facial mask.

DETAILED DESCRIPTION

To illustrate the present invention more clearly, the present invention will be further described below with reference to the preferred examples. Those skilled in the art should understand that the content specifically described below is illustrative, not restrictive, and should not be used to limit the protection scope of the present invention.

All numerical designations in the present invention (e.g., temperature, time, concentration and weight or mass, including the range of each) may generally be approximate values of (+) or (−) in increments of 0.1 or 1.0, as appropriate. All numerical designations are understood to be preceded by the term "about".

Example 1

Figure 1A:
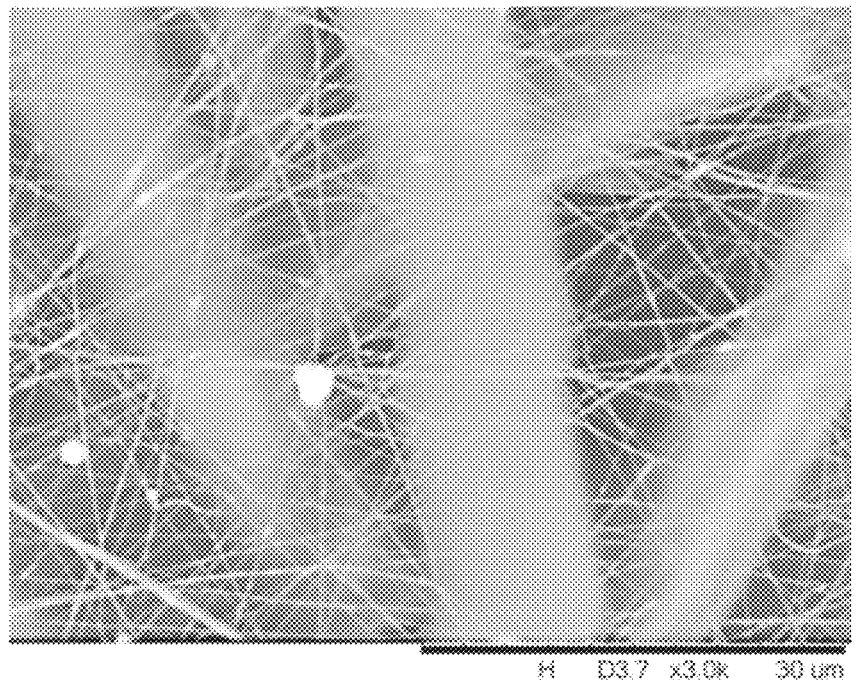
FIGS. 1a and 1b are scanning electron microscope images of the hydrophobic surface of the facial mask obtained in Example 1 of the present invention.
Figure 1B:
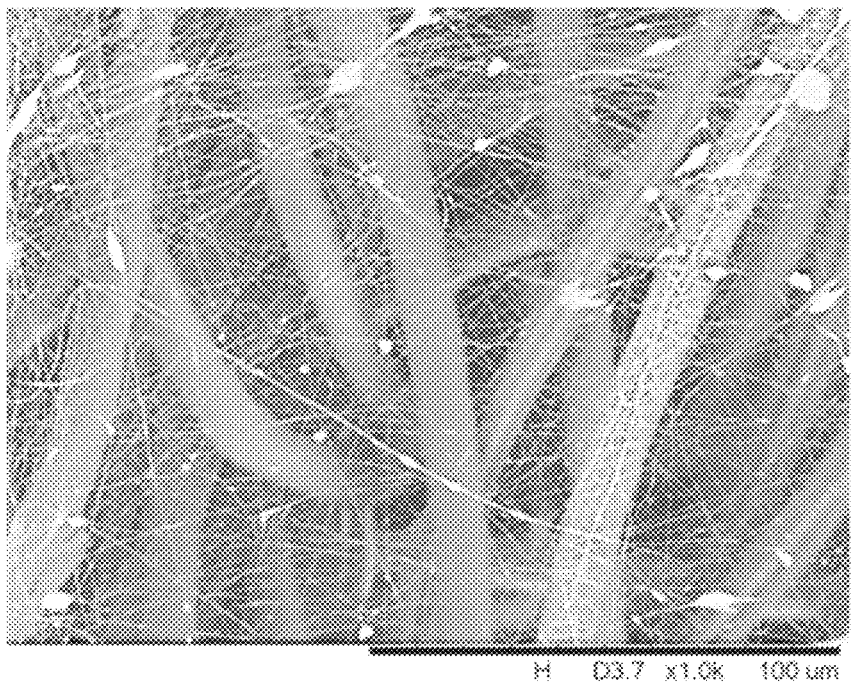

A water-soluble unidirectional moisture transport traditional Chinese medicine facial mask is prepared in the present example, including the following steps:
(1) Preparation of a Spinning Stock Solution A:

5 g of hydrophobic PVDF and 0.1 g of lithium chloride powder were added to 20 g of a dimethylformamide (DMF) organic solvent and stirred at 40° C. for 2 h. Then 1 g of fluorinated silica aerogel powder was dispersed in the resulting solution, and the solution was ultrasonically dispersed for 30 min and stirred at room temperature for 1 h. Finally, a high-viscosity and transparent spinning stock solution A was obtained and placed at room temperature for later use.
(2) Preparation of a Hydrophobic Layer:

A superhydrophilic substrate used as a collecting substrate was wrapped on a roller. The spinning stock solution A obtained in step (1) was collected on the superhydrophilic non-woven fabric substrate under a high voltage of 18 kV by means of a single-needle spinning device, and a hydrophobic electrospun fiber layer was prepared and obtained, wherein the injection pump flow rate was set as 0.2 mL/h, the receiving distance was 5 cm, and the spinning time was 30 min. Finally, it was removed from the roller and placed at room temperature for later use. The scanning electron microscope images are shown in FIGS. 1a and 1b. It can be seen that the PVDF electrospun nanofibers are randomly and irregularly spread on the surface of the fiber substrate and form a porous fiber membrane. The white particles are superhydrophobic silica aerogel particles dispersed therein.
(3) Preparation of an Electrostatic Spraying Stock Solution B Containing Traditional Chinese Medicine Ingredients:

4 g of *Bletilla striata* gel, 1 g of rose essential oil, 1 g of ethylene glycol, 0.1 g of hyaluronic acid, 0.1 g of sodium hexadecyl sulfonate and 0.1 g of lithium chloride powder were dispersed in 20 mL of distilled water and stirred at room temperature for 2 h to obtain the spraying stock solution B.
(4) Preparation of an Electro-Sprayed Layer (Facial Mask Effective Ingredient Layer) Containing the Traditional Chinese Medicine Ingredients:

The opposite side of the superhydrophilic non-woven fabric substrate with the PVDF hydrophobic layer obtained in step (2) was wrapped on an electrostatic spraying roller, with the superhydrophilic surface facing outward. The spraying stock solution B obtained in step (3) was collected on the superhydrophilic substrate under a high voltage of 20 kV by means of a single-needle spinning device, and a sprayed layer containing the traditional Chinese medicine ingredients was prepared and obtained, wherein the injection pump flow rate was set as 0.4 mL/h, the receiving distance was 12 cm, and the spraying time was 5 min. Finally, the entity was removed from the roller and placed in an oven at 60° C. for 24 h for drying.

Example 2

A water-soluble unidirectional moisture transport traditional Chinese medicine facial mask is prepared in the present example, including the following steps:

(1) Preparation of a Spinning Stock Solution A:

3 g of hydrophobic PVDF and 0.1 g of lithium chloride powder were added to 20 g of a dimethylformamide (DMF) organic solvent and stirred at 40° C. for 4 h. Then 4 g of fluorinated silica aerogel powder was dispersed in the resulting solution, and the solution was ultrasonically dispersed for 60 min and stirred at room temperature for 2 h. Finally, a high-viscosity and transparent spinning stock solution A was obtained and placed at room temperature for later use.

(2) Preparation of a Hydrophobic Layer:

A superhydrophilic substrate used as a collecting substrate was wrapped on a roller. The spinning stock solution A obtained in step (1) was collected on the superhydrophilic non-woven fabric substrate under a high voltage of 22 kV by means of a single-needle spinning device, and a hydrophobic electrospun fiber layer was prepared and obtained, wherein the injection pump flow rate was set as 0.1 mL/h, the receiving distance was 10 cm, and the spinning time was 60 min. Finally, it was removed from the roller and placed at room temperature for later use.

Figure 2A:
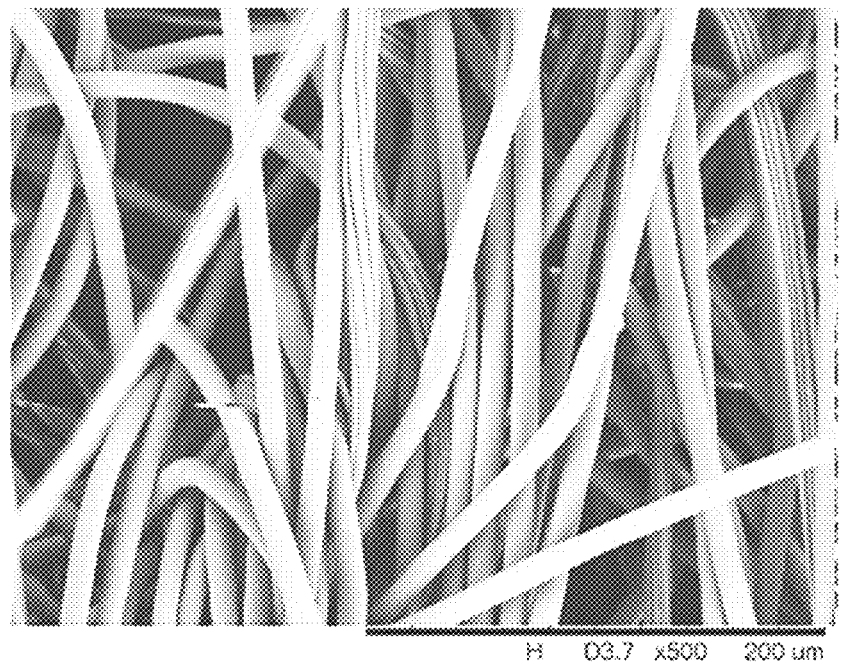
FIGS. 2a and 2b are scanning electron microscope images of the hydrophilic substrate in the facial mask obtained in Example 2 of the present invention.
Figure 2B:
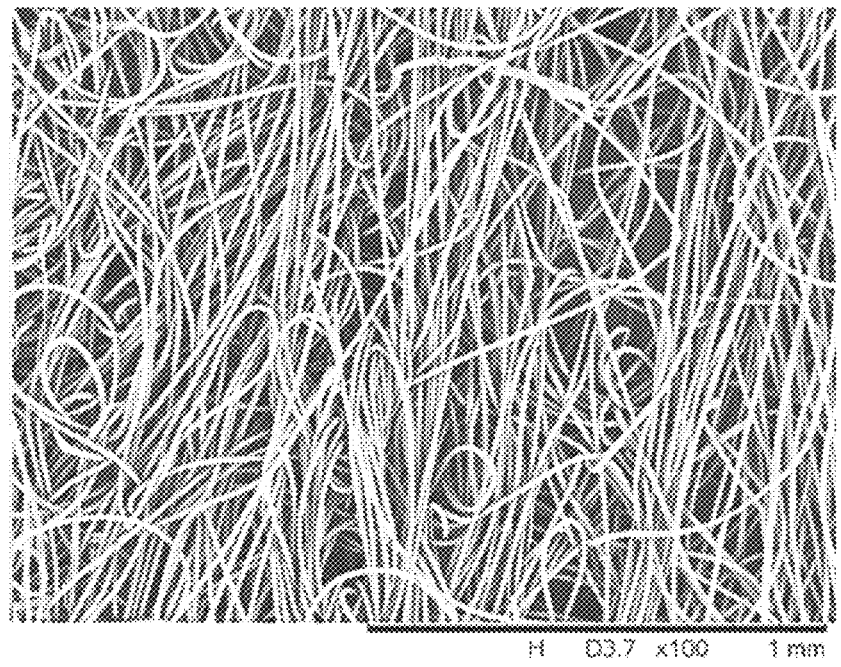

The scanning electron microscope images of the superhydrophilic substrate used are shown in FIGS. 2a and 2b. It can be seen that the superhydrophilic substrate is composed of dense coarse fibers with a diameter of about 10-15 μm.

(3) Preparation of an Electrostatic Spraying Stock Solution B Containing Traditional Chinese Medicine Ingredients:

2 g of *Bletilla striata* gel, 1 g of tea tree essential oil, 1 g of glycerol, 0.1 g of hyaluronic acid, 0.05 g of sodium hexadecyl sulfonate and 0.1 g of lithium chloride powder were dispersed in 20 mL of distilled water and stirred at room temperature for 1 h to obtain the spraying stock solution B.

(4) Preparation of an Electro-Sprayed Layer Containing the Traditional Chinese Medicine Ingredients:

The opposite side of the superhydrophilic non-woven fabric substrate with the PVDF hydrophobic layer obtained in step (2) was wrapped on an electrostatic spraying roller, with the superhydrophilic surface facing outward. The spraying stock solution B obtained in step (3) was collected on the superhydrophilic substrate under a high voltage of 22 kV by means of a single-needle spinning device, and a sprayed layer containing the traditional Chinese medicine ingredients was prepared and obtained, wherein the injection pump flow rate was set as 0.2 mL/h, the receiving distance was 15 cm, and the spraying time was 30 min. Finally, the entity was removed from the roller and placed in an oven at 60° C. for 24 h for drying.

Example 3

A water-soluble unidirectional moisture transport traditional Chinese medicine facial mask is prepared in the present example, including the following steps:

(1) Preparation of a Spinning Stock Solution A:

4 g of hydrophobic TPU and 0.1 g of lithium chloride powder were added to 20 g of a dimethylformamide (DMF) organic solvent and stirred at 60° C. for 2 h. Then 2 g of fluorinated silica aerogel powder was dispersed in the resulting solution, and the solution was ultrasonically dispersed for 40 min and stirred at room temperature for 2 h. Finally, a high-viscosity and transparent spinning stock solution A was obtained and placed at room temperature for later use.

(2) Preparation of a Hydrophobic Layer:

A superhydrophilic substrate used as a collecting substrate was wrapped on a roller. The spinning stock solution A obtained in step (1) was collected on the superhydrophilic non-woven fabric substrate under a high voltage of 26 kV by means of a single-needle spinning device, and a hydrophobic electrospun fiber layer was prepared and obtained, wherein the injection pump flow rate was set as 0.3 mL/h, the receiving distance was 10 cm, and the spinning time was 120 min. Finally, it was removed from the roller and placed at room temperature for later use.

(3) Preparation of an Electrostatic Spraying Stock Solution B Containing Traditional Chinese Medicine Ingredients:

2 g of *Bletilla striata* gel, 1 g of lavender essential oil, 1 g of butanediol, 0.1 g of hyaluronic acid, 0.05 g of sodium lauryl polyoxyethylene ether sulfate and 0.05 g of lithium chloride powder were dispersed in 20 mL of distilled water and stirred at room temperature for 2 h to obtain the spraying stock solution B.

Figure 3A:
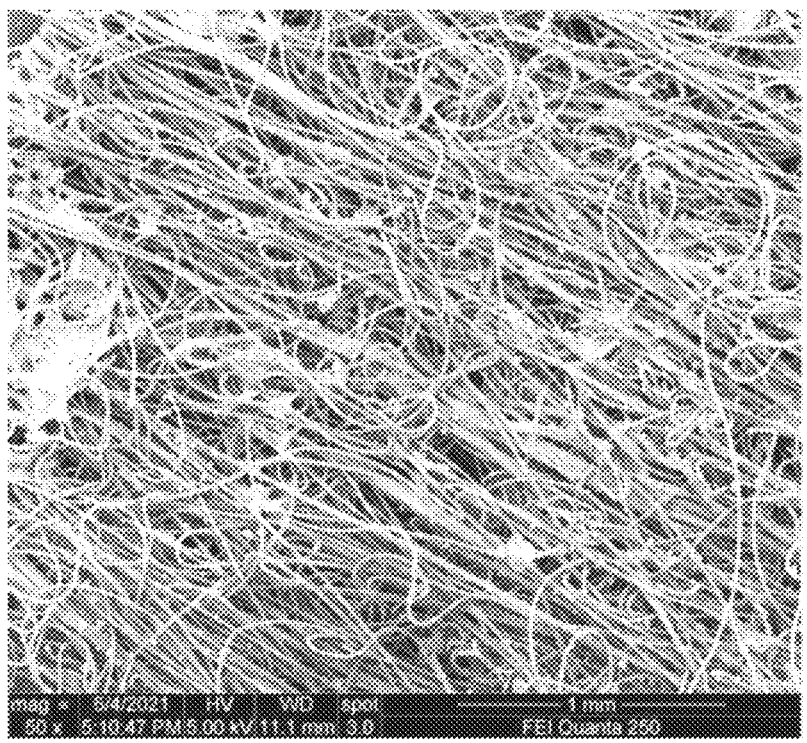
FIGS. 3a and 3b are scanning electron microscope images of the facial mask effective ingredient layer of the facial mask obtained in Example 3 of the present invention.
Figure 3B:
Figure 4A:
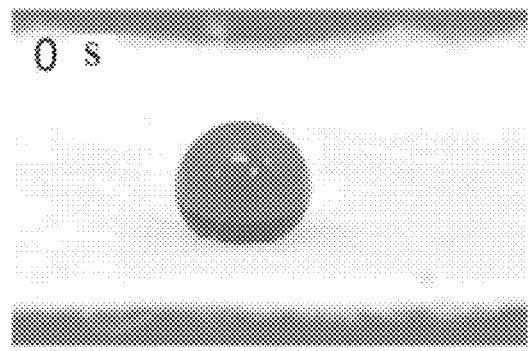
FIGS. 4a to 4d are photographs of the unidirectional moisture transport process of the facial mask obtained in Example 4 of the present invention.
Figure 4B:
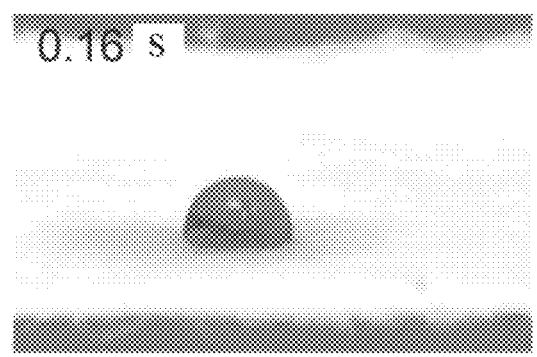
Figure 4C:
Figure 4D:
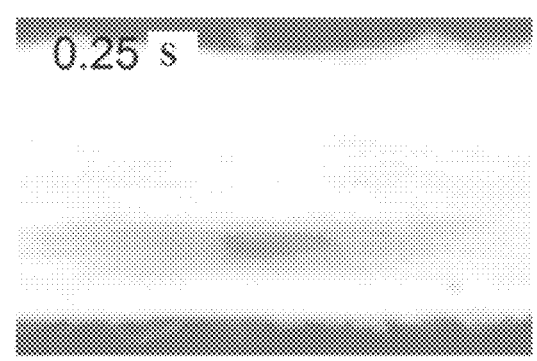

(4) Preparation of an Electro-Sprayed Layer Containing the Traditional Chinese Medicine Ingredients:

The opposite side of the superhydrophilic non-woven fabric substrate with the TPU hydrophobic layer obtained in step (2) was wrapped on an electrostatic spraying roller, with the superhydrophilic surface facing outward. The stock solution B obtained in step (3) was collected on the superhydrophilic non-woven fabric substrate under a high voltage of 26 kV by means of a single-needle spinning device, and a sprayed layer containing the traditional Chinese medicine ingredients was prepared and obtained, wherein the injection pump flow rate was set as 0.4 mL/h, the receiving distance was 15 cm, and the spraying time was 20 min. Finally, the entity was removed from the roller and placed in an oven at 60° C. for 36 h for drying. The scanning electron microscope images are shown in FIGS. 3a and 3b. It can be seen that the effective ingredients of the traditional Chinese medicine colloid were randomly and irregularly sprayed all over the surface of the fiber substrate, forming membrane or particle structures of different sizes, and were well attached to the substrate surface.

Example 4

A water-soluble unidirectional moisture transport traditional Chinese medicine facial mask is prepared in the present example, including the following steps:

(1) Preparation of a Spinning Stock Solution A:

2 g of hydrophobic TPU and 0.2 g of lithium chloride powder were added to 20 g of a dimethylformamide (DMF) organic solvent and stirred at 60° C. for 2 h. Then 4 g of fluorinated silica aerogel powder was dispersed in the resulting solution, and the solution was ultrasonically dispersed for 60 min and stirred at room temperature for 2 h. Finally, a high-viscosity and transparent spinning stock solution A was obtained and placed at room temperature for later use.

(2) Preparation of a Hydrophobic Layer:

A superhydrophilic cellulose membrane used as a collecting substrate was wrapped on a roller. The stock solution A obtained in step (1) was collected on the superhydrophilic cellulose membrane substrate under a high voltage of 20 kV by means of a single-needle spinning device, and a hydrophobic electrospun fiber layer was prepared and obtained, wherein the injection pump flow rate was set as 0.3 mL/h, the receiving distance was 10 cm, and the spinning time was 60 min. Finally, it was removed from the roller and placed at room temperature for later use.

(3) Preparation of an Electrostatic Spraying Stock Solution B Containing Traditional Chinese Medicine Ingredients:

2 g of *Bletilla striata* gel, 1 g of lavender essential oil, 1 g of propanediol, 0.1 g of hyaluronic acid, 0.05 g of sodium lauryl polyoxyethylene ether sulfate and 0.1 g of lithium chloride powder were dispersed in 20 mL of distilled water and stirred at room temperature for 2 h to obtain the spraying stock solution B.

(4) Preparation of an Electro-Sprayed Layer Containing the Traditional Chinese Medicine Ingredients:

The opposite side of the superhydrophilic cellulose membrane with the TPU hydrophobic layer obtained in step (2) was wrapped on an electrostatic spraying roller, with the superhydrophilic surface facing outward. The stock solution B obtained in step (3) was collected on the superhydrophilic cellulose membrane substrate under a high voltage of 20 kV by means of a single-needle spinning device, and a sprayed layer containing the traditional Chinese medicine ingredients was prepared and obtained, wherein the injection pump flow rate was set as 0.3 mL/h, the receiving distance was 15 cm, and the spraying time was 10 min. Finally, the entity was removed from the roller and placed in an oven at 60° C. for 24 h for drying.

(5) Test for the Ability of Unidirectional Moisture Transport:

When a blue water droplet was dropped onto the hydrophobic surface of the facial mask obtained in step (4), the droplet existed in a spherical shape for a short time, and then was quickly absorbed into the lower superhydrophilic substrate, while the hydrophobic surface remained dry. The process is shown in FIGS. 4a to 4d, which proves that the facial mask has the ability of unidirectional moisture transport.

(6) Dissolution of Effective Ingredients

Figure 5:
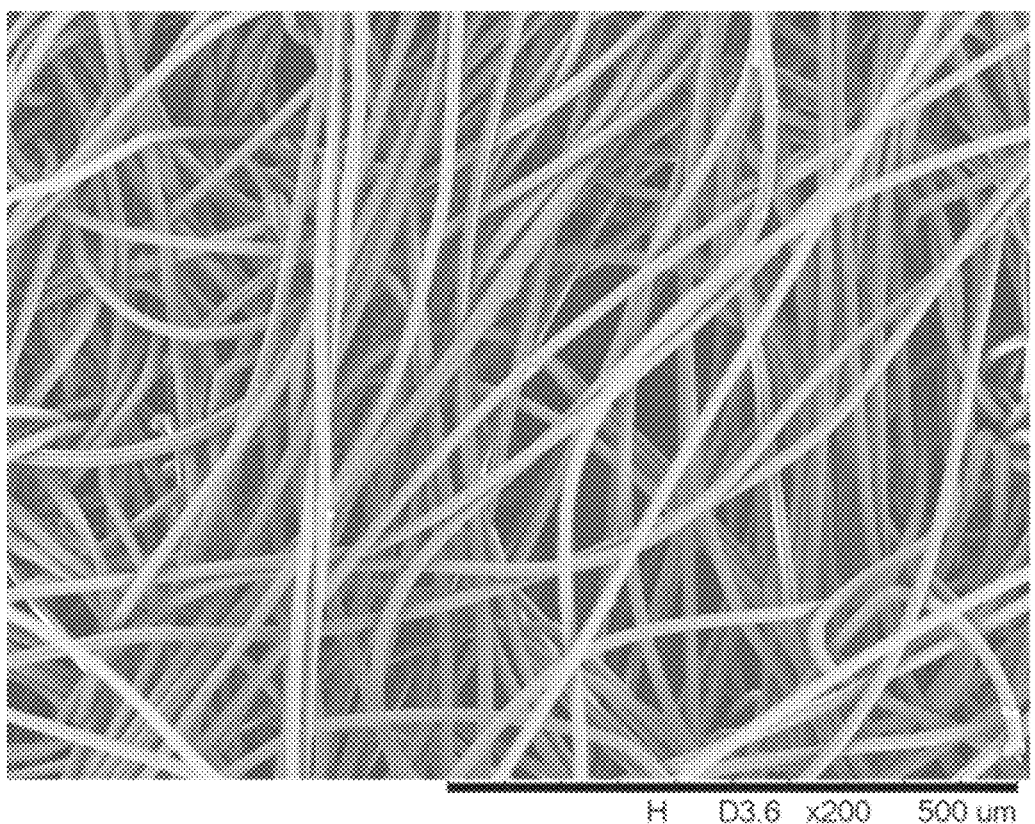
FIG. 5 is an electron microscope image of the facial mask after immersion in water in step (6) of Example 4.

The entire facial mask obtained in step (4) was immersed in water and taken out immediately after 5 s, and dried in an oven at 40° C. for 3 h until completely dried. The surface of the facial mask containing the traditional Chinese medicine effective ingredients was observed under an electron microscope, and the results are shown in FIG. 5. It was found that the irregular membranes or particles containing the traditional Chinese medicine effective ingredients on the surface of the substrate completely disappeared, indicating that the effective ingredients could be completely dissolved in water in a short time.

Example 5

A water-soluble unidirectional moisture transport traditional Chinese medicine facial mask is prepared in the present example, including the following steps:

(1) Preparation of a Spinning Stock Solution A:

2 g of hydrophobic TPU and 0.2 g of lithium chloride powder were added to 20 g of a tetrahydrofuran organic solvent and stirred at 60° C. for 2 h. Finally, a high-viscosity and transparent spinning stock solution A was obtained and placed at room temperature for later use.

(2) Preparation of a Hydrophobic Layer:

A superhydrophilic cellulose membrane used as a collecting substrate was wrapped on a roller. The stock solution A obtained in step (1) was collected on the superhydrophilic cellulose membrane substrate under a high voltage of 24 kV by means of a single-needle spinning device, and a hydrophobic electrospun fiber layer was prepared and obtained, wherein the injection pump for rate was set as 0.2 mL/h, the receiving distance was 10 cm, and the spinning time was 60 min. Finally, it was removed from the roller and placed at room temperature for later use.

(3) Preparation of an Electrostatic Spraying Stock Solution B Containing Traditional Chinese Medicine Ingredients:

2 g of *Bletilla striata* gel, 1 g of lavender essential oil, 1 g of propanediol, 0.1 g of hyaluronic acid, 0.05 g of sodium lauryl polyoxyethylene ether sulfate and 0.1 g of lithium chloride powder were dispersed in 20 mL of distilled water and stirred at room temperature for 2 h to obtain the spraying stock solution B.

(4) Preparation of an Electro-Sprayed Layer Containing the Traditional Chinese Medicine Ingredients:

The opposite side of the superhydrophilic cellulose membrane with the TPU hydrophobic layer obtained in step (2) was wrapped on an electrostatic spraying roller, with the superhydrophilic surface facing outward. The stock solution B obtained in step (3) was collected on the superhydrophilic cellulose membrane substrate under a high voltage of 20 kV by means of a single-needle spinning device, and a sprayed layer containing the traditional Chinese medicine ingredients was prepared and obtained, wherein the injection pump flow rate was set as 0.3 mL/h, the receiving distance was 12 cm, and the spraying time was 30 min. Finally, the entity was removed from the roller and placed in an oven at 50° C. for 20 h for drying.

(5) Test for the Ability of Unidirectional Moisture Transport:

When a blue water droplet was dropped onto the hydrophobic surface of the facial mask obtained in step (4), the droplet existed in a spherical shape for a short time, and then was quickly absorbed into the lower superhydrophilic substrate, while the hydrophobic surface remained dry, which proves that the facial mask has the ability of unidirectional moisture transport.

Example 6

A water-soluble unidirectional moisture transport traditional Chinese medicine facial mask is prepared in the present example, including the following steps:

(1) Preparation of a Spinning Stock Solution A:

4 g of hydrophobic TPU and 0.1 g of lithium chloride powder were added to 20 g of a dimethylformamide (DMF) organic solvent and stirred at 60° C. for 2 h. Then 1.5 g of superhydrophobic stearic acid-magnesium oxide powder was dispersed in the resulting solution, and the solution was ultrasonically dispersed for 60 min and stirred at room temperature for 1 h. Finally, a high-viscosity and transparent spinning stock solution A was obtained and placed at room temperature for later use.

(2) Preparation of a Hydrophobic Layer:

A superhydrophilic substrate used as a collecting substrate was wrapped on a roller. The spinning stock solution A obtained in step (1) was collected on the superhydrophilic non-woven fabric substrate under a high voltage of 26 kV by means of a single-needle spinning device, and a hydrophobic electrospun fiber layer was prepared and obtained, wherein the injection pump flow rate was set as 0.3 mL/h, the receiving distance was 12 cm, and the spinning time was 120 min. Finally, it was removed from the roller and placed at room temperature for later use.

(3) Preparation of an Electrostatic Spraying Stock Solution B Containing Traditional Chinese Medicine Ingredients:

2 g of *Bletilla striata* gel, 1 g of lavender essential oil, 1 g of butanediol, 0.1 g of hyaluronic acid, 0.05 g of sodium lauryl polyoxyethylene ether sulfate and 0.05 g of lithium chloride powder were dispersed in 20 mL of distilled water and stirred at room temperature for 2 h to obtain the spraying stock solution B.

(4) Preparation of an Electro-Sprayed Layer Containing the Traditional Chinese Medicine Ingredients:

The opposite side of the superhydrophilic non-woven fabric substrate with the TPU hydrophobic layer obtained in step (2) was wrapped on an electrostatic spraying roller, with the superhydrophilic surface facing outward. The stock solution B obtained in step (3) was collected on the superhydrophilic non-woven fabric substrate under a high voltage of 26 kV by means of a single-needle spinning device, and a sprayed layer containing the traditional Chinese medicine ingredients was prepared and obtained, wherein the injection pump flow rate was set as 0.25 mL/h, the receiving distance was 12 cm, and the spraying time was 40 min. Finally, the entity was removed from the roller and placed in an oven at 60° C. for 32 h for drying.

The above examples of the present invention are only examples for clearly illustrating the present invention, but are not intended to limit the embodiments of the present invention. For those of ordinary skill in the art, other different forms of changes or variations may also be made on the basis of the above description. It is impossible to list all the embodiments here. Any obvious changes or variations derived from the technical solutions of the present invention are still within the protection scope of the present invention.

The invention claimed is:

1. A dry facial mask, comprising:
a superhydrophilic substrate including a first lateral surface and a second lateral surface;
a hydrophobic layer provided on the first lateral surface of the superhydrophilic substrate; and
a facial mask effective ingredient comprising a traditional Chinese medicine colloid of *Bletilla striata* gel loaded to the second lateral surface, wherein the facial mask effective ingredient further comprises a plant essential oil, a moisturizing agent, hyaluronic acid, a surfactant and a metal salt, wherein a mass ratio of the traditional Chinese medicine colloid to the plant essential oil to the moisturizing agent to the hyaluronic acid to the surfactant to the metal salt is (20-40):(5-10):(2-10):1:(0.2-2):(0.5-1), wherein the facial mask effective ingredient is provided on the second lateral surface of the superhydrophilic substrate in the form of a dried dispersed membrane structure or a dried dispersed particle structure; and the facial mask effective ingredient is dissolvable in water for unidirectional transport away from the second lateral surface.

2. The dry facial mask according to claim 1, wherein the superhydrophilic substrate is a cellulose membrane or a superhydrophilic non-woven fabric.

3. The dry facial mask according to claim 1, wherein the plant essential oil is selected from the group consisting of rose essential oil, tea tree essential oil, lavender essential oil, and grapefruit essential oil and a combination thereof.

4. The dry facial mask according to claim 1, wherein the moisturizing agent is selected from the group consisting of glycerol, butanediol, and propylene glycol and a combination thereof.

5. The dry facial mask according to claim 1, wherein the surfactant is selected from the group consisting of sodium hexadecyl sulfonate, sodium lauryl polyoxyethylene ether sulfate, and coconate diethanolamide and a combination thereof.

6. The dry facial mask according to claim 1, wherein the metal salt is lithium chloride and/or sodium chloride.

7. A preparation method of the dry facial mask according to claim 1, comprising:
forming the hydrophobic layer by electrospinning on the first lateral surface of the superhydrophilic substrate;
preparing the facial mask effective ingredient on the second lateral surface of the superhydrophilic substrate; and
heating and drying to obtain the dry facial mask.

8. The preparation method according to claim 7, wherein the facial mask effective ingredient is prepared by electrostatic spraying.

9. The preparation method according to claim 8, wherein preparing the facial mask effective ingredient comprises:
adding the facial mask effective ingredient into water to form an electrostatic spraying stock solution; and
wrapping the superhydrophilic substrate on an electrostatic spraying roller with the superhydrophilic surface facing outward, and electrostatically spraying the electrostatic spraying stock solution on the superhydrophilic surface of the superhydrophilic substrate to disperse the facial mask effective ingredient.

10. The preparation method according to claim 9, wherein the mass ratio of the metal salt in the facial mask effective ingredient to water is (0.5-1):200.

11. The preparation method according to claim 9, wherein the electrostatic spraying is performed by a single-needle electrostatic spraying device.

12. The preparation method according to claim 9, wherein conditions of the electrostatic spraying comprise: a voltage of 18-30 kV, an injection pump flow rate of 0.1-0.4 mL/h, and a receiving distance of 5-15 cm.

13. The preparation method according to claim 7, wherein the preparation of the hydrophobic layer comprises:
adding a hydrophobic polymer and the metal salt into a dimethylformamide (DMF) and/or tetrahydrofuran solvent, in which a superhydrophobic powder is dispersed to obtain a spinning stock solution; and
wrapping the superhydrophilic substrate on a roller, and preparing the hydrophobic layer by electrospinning the spinning stock solution on the superhydrophilic substrate.

14. The preparation method according to claim 13, wherein the electrospinning is performed by a single-needle spinning device.

15. The preparation method according to claim 13, wherein conditions of the electrospinning comprise: a voltage of 18-26 kV, an injection pump flow rate of 0.1-0.4 mL/h, and a receiving distance of 10-15 cm.

16. The preparation method according to claim 13, wherein the hydrophobic polymer is polyurethane and/or polyvinylidene fluoride.

17. The preparation method according to claim 13, wherein the metal salt is lithium chloride and/or sodium chloride.

18. The preparation method according to claim 13, wherein the superhydrophobic powder is superhydrophobic silica aerogel powder or stearic acid-magnesium oxide powder.

19. The preparation method according to claim 13, wherein the mass ratio of the hydrophobic polymer to the superhydrophobic powder to the metal salt to the solvent is (2-5):(0-4):(0.05-0.2):20.

20. The dry facial mask according to claim 1, wherein the hydrophobic layer comprises electrospun fibers of hydrophobic polymer selected from the group consisting of polyurethane and polyvinylidene fluoride and a combination thereof.

21. The dry facial mask according to claim 20, wherein the hydrophobic layer further comprises a superhydrophobic powder selected from the group consisting of a superhydrophobic silica aerogel powder and a stearic acid-magnesium oxide powder.

* * * * *